United States Patent
Abrahamian et al.

(10) Patent No.: US 7,580,799 B2
(45) Date of Patent: Aug. 25, 2009

(54) METHOD FOR CHARACTERIZING AND ANALYZING 3-D SHAPES OF MOLECULES UTILIZING STERIC MULTIPLETS

(76) Inventors: Edmond Abrahamian, 1119 Moorlands Dr., Richmond Heights, MO (US) 63117; Robert D. Clark, 827 Renee La., Creve Coeur, MO (US) 63141; Peter Fox, 506 S. Old Orchard Ave., Webster Groves, MO (US) 63119; Essam Metwally, 970 N. Spoede Rd. #27, St. Louis, MO (US) 63146

( * ) Notice: Subject to any disclaimer, the term of this patent is extended or adjusted under 35 U.S.C. 154(b) by 207 days.

(21) Appl. No.: 11/799,037

(22) Filed: Apr. 30, 2007

(65) Prior Publication Data

US 2008/0071478 A1    Mar. 20, 2008

Related U.S. Application Data

(63) Continuation of application No. 10/926,781, filed on Aug. 25, 2004, now Pat. No. 7,212,951.

(51) Int. Cl.
    *G06F 19/00* (2006.01)
(52) U.S. Cl. .............. 702/27; 702/19; 702/22; 702/23; 702/150; 702/153; 702/152; 703/11
(58) Field of Classification Search .......... 702/19, 702/22, 23, 27, 150, 152, 153; 703/11
    See application file for complete search history.

(56) References Cited

U.S. PATENT DOCUMENTS

| | | | | |
|---|---|---|---|---|
| 4,333,165 A * | 6/1982 | Swainson et al. | ........... | 365/120 |
| 5,555,366 A * | 9/1996 | Teig et al. | ........... | 711/169 |
| 5,784,294 A * | 7/1998 | Platt et al. | ........... | 702/27 |
| 6,208,942 B1 * | 3/2001 | Hurst et al. | ........... | 702/27 |
| 6,671,626 B2 * | 12/2003 | Silverman | ........... | 702/27 |
| 7,356,415 B1 * | 4/2008 | Pitman et al. | ........... | 702/19 |
| 2004/0082074 A1 * | 4/2004 | McGrath | ........... | 436/171 |
| 2005/0007367 A1 * | 1/2005 | Morikawa | ........... | 345/441 |
| 2005/0119834 A1 * | 6/2005 | Kita et al. | ........... | 702/19 |
| 2005/0119837 A1 * | 6/2005 | Prakash et al. | ........... | 702/27 |
| 2005/0228592 A1 * | 10/2005 | Ahuja et al. | ........... | 702/19 |

* cited by examiner

*Primary Examiner*—Carol S Tsai
(74) *Attorney, Agent, or Firm*—Laurence Weinberger

(57) ABSTRACT

Steric features inherent in the three dimensional disposition of atoms in molecules can be represented as multiplets using a defined set of steric descriptors. The resulting multiplets can be encoded in a compressed form of bitstring known as a bitmap. Such bitmaps can be generated in compressed form and used to compare individual conformers or ensembles of conformers of molecules to each other without decompression. Such comparisons are useful in molecular similarity analysis, in molecular diversity analysis, in database searching, and in conformational analysis.

2 Claims, 1 Drawing Sheet

US 7,580,799 B2

METHOD FOR CHARACTERIZING AND ANALYZING 3-D SHAPES OF MOLECULES UTILIZING STERIC MULTIPLETS

This Application is a continuation of application Ser. No. 10/926,781 filed Aug. 25, 2004 due to issue May 1, 2007 as U.S. Pat. No. 7,212,951.

FIELD OF THE INVENTION

The invention involves a novel computer implemented method for characterizing and analyzing the 3-D shapes of molecules. More specifically, the three-dimensional shapes of molecules are characterized in such a way that the characterizing descriptor created can effectively be used to compare individual conformers or ensembles of conformers of molecules to each other. The comparison obtained thereby is demonstrably useful in molecular similarity analysis, in molecular diversity analysis, in database searching, and in conformational analysis particularly in the drug discovery area.

BACKGROUND OF THE INVENTION

That potent and selective enzyme inhibitors must fit snugly into their respective binding sites has been recognized since Emil Fischer first formulated his "Lock & Key" hypothesis in 1895, with the idea having been extended since to interactions between agonists and antagonists with their target receptors. Researchers subsequently came to appreciate that complementary shapes alone are not enough to confer potency—that the natures of the juxtaposed surfaces must also be more or less complementary. This added dimension led to the realization that ligands that bind tightly to a particular target often share groups of localized interaction features—hydrogen bond donors and acceptors, as well as hydrophobic and ionized groups. Moreover, it was recognized that those groups of localized interaction features tend to be arrayed in a specific pattern in three-dimensional space, provided the ligand in question has been put into its binding conformation[1]. This concept was widely disseminated after 1970. The three dimensional spatial distribution of the localized interaction features has been commonly referred to as a pharmacophore or pharmacophore pattern. Subsequently, software was designed to find pharmacophore patterns shared among groups of flexible analog molecules active against a common target[2] and to use such patterns as 3-D search queries to identify additional candidate molecules for testing[3] and further drug development.

Until recently, pharmacophore identification and searching have focused primarily on such feature complementarity, and to some degree the broader notion of shape complementarity underlying the lock-and-key hypothesis has been set aside. Progress in the area of computer implemented in silico docking made in the last several years, however, has served to re-emphasize the importance of minimizing surface mismatches between ligands and their binding sites.[4] In the area of pharmacophore searching, this has resulted in the inclusion of exclusion volume constraints into queries derived from X-ray crystallographic data.[5,6] The same approach can, in principle, be used for binding site structures based on homology modelling, though such structures are rarely precisely enough defined for this to be a practical approach.

However, exclusion volumes suffer from some rather severe limitations in their ability to encapsulate steric information. In particular, they represent intrinsically negative boundary constraints. Worse yet, optimal solutions are represented by snug fits, where ligand atoms lie as close as possible to an exclusion surface approximated by an ensemble of exclusion volumes, rather than as far as possible away from those surfaces. Unfortunately, such sharply bounded negative constraints are ill-suited for incorporation into efficient search methods based on genetic algorithms, steepest descent, simplex or directed tweak methods.[7]

In addition, exclusion volumes do not adequately reflect the plasticity of most binding sites, where some kind of partial match constraint would more appropriately reflect the observed dynamic nature of the interactions involved. The shape of the binding site "lock" usually changes to a greater or lesser extent depending on the exact nature of the ligand "key."

Pharmacophore Multiplets:

Pharmacophore multiplet fingerprints were originally developed for assessing molecular diversity[8,9] and were subsequently applied to assess molecular similarity.[10] Such fingerprints capture the spatial relationship between features by decomposing the complete pharmacophoric pattern of a molecule into its constituent k-tuples of features—an ensemble of pairs, triplets and quartets, where k=2, 3 or 4, respectively. For f features, the maximum number $M_{max}$ of such constituent elements (multiplets) is given by:

$$M_{max} = \frac{f!}{k!(f-k)!}.$$

By characterizing each possible multiplet as a colored graph (i.e., by the feature types involved (vertex colors) and the binned inter-feature distances (edge lengths)) it is possible to construct a bitstring (fingerprint) in which a particular bit is 1 if the corresponding pharmacophore multiplet was found in a molecular conformation of interest and is 0 otherwise. Comparing such fingerprints to each other then provides a quantitative measure of the pharmacophoric similarity of the molecules from which the fingerprints were generated. The number of distinct multiplets actually found in a given structure may be (and usually is) less than $M_{max}$ due to symmetry, because of limitations in the coarseness of the feature type categorization or because the granularity of edge length binning used is finite, or some combination thereof.

In early work on pharmacophoric diversity, the principal focus was on identifying unique pharmacophoric elements for preferential incorporation into combinatorial library designs.[11] For such applications, it makes sense to examine multiple conformers for each molecule of interest and set a fingerprint bit if the corresponding multiplet is found in any conformation; this is mathematically equivalent to applying a Boolean OR (union) across the fingerprint obtained for each conformation. For similarity applications, better discrimination can be obtained in some cases by using count vectors rather than bitstring fingerprints; in such applications, each count can reflect the number of conformations in which each multiplet is found. Alternatively, the count can correspond to the number of occurrences in each conformation summed across all conformations considered. In general it is more efficient to generate and use compressed bitstrings (bitmaps) or compressed count vectors.

By examining a set of bitmaps derived from a collection of effective ligands which bind to a common target, it is possible to pick out bits corresponding to highly discriminating pharmacophore multiplets shared by an unexpectedly large fraction of the ligands. The bits set by these shared multiplets can then be used to construct an hypothesis bitmap that can be useful in screening virtual databases for ligands whose bitmaps are especially similar to the hypothesis.[22] By construction, such hypotheses readily encompass partial match constraints, since fingerprints can be similar even if not identical. It is very unlikely that any candidate molecule/potential ligand will present all multiplets encoded in the query; it is enough that most of them are found in a potential ligand, and that the number of extraneous multiplets not be too large.

Applicants are unaware of any scientific literature that describes or anticipates the invention disclosed in this patent document. Additionally, applicants searched the USPTO database for abstracts containing the terms "molecular" and "shape". A total of 386 hits were examined.

Silverman in U.S. Pat. No. 6,671,626 (Determination and use of three-dimensional moments of molecular property fields) and D. E. Platt & B. D. Silverman in U.S. Pat. No. 5,784,294 (System and method for comparative molecular moment analysis [CoMMA]} deal with the use of steric molecular moments to characterize molecules. These make use of every atom, hydrogen and non-hydrogen, in the molecule of interest, and characterize their distribution in space by a series of moments calculated from the full aggregate. The terms in such a characterization contain little or no local information about the structure and are not amenable to dynamic interpretation, i.e., cannot be averaged usefully across the ensemble of possible conformations that a flexible molecule can take on. The extracted moments, like harmonics, are aggregate properties derived from the whole molecule.

The two CoMFA patents of Cramer and Wold, U.S. Pat. Nos. 5,307,287 and 5,025,388 (Comparative molecular field analysis), involve point-by-point comparisons between molecular fields calculated on a Cartesian lattice into which each molecule has been placed. Again, such comparisons are only meaningful when a single conformation is specified for each molecule and both molecules of interest must be embedded in a common frame of reference. Related techniques have subsequently been described for identifying canonical conformations and orientations for generalizing such comparisons,[12,13,14] but these cannot account for molecular flexibility and are not based on molecular connectivity.

In U.S. Pat. No. 6,182,016 (Molecular classification for property prediction) Liang and Edelsbrunner teach a topologically based approach that is primarily local in nature. The technology they describe involves characterizing a Voronoi partition[15] of each molecule by applying a Delaunay triangulation[16] to the heavy atoms in that molecule. This transforms each molecule into an assemblage of terahedra (mostly from quaternary carbon, nitrogen, phosphorous and sulfur), triangles (mostly tertiary carbon, nitrogen, and sulfur), and isolated edges (from other bonded heavy atom pairs). The invention's descriptor is then constructed as a list of the topological elements found in the molecule of interest and their frequencies. When greater resolution is desired, properties are attached to the toplogical elements by indicating the elemental types of the various atoms comprising them. Each topological element can also be characterized by the types of topological elements adjoined to them in the Delaunay triangulation and how they are adjoined; two tetrahedra, for example, can be joined corner to corner, edge to edge, or face to face.

The invention described in this patent document does take topological factors into account when deciding which heavy atoms and combinations thereof should be used to define steric features, but unlike Lang and Edelsbrunner, it does not utilize local toplogical elements in constructing its descriptors. Rather, the spatial relationship between the steric features is characterized in terms of all triangles (triplets) or tetrahedra (quartets) formed among them.

The Liang and Edelsbrunner patent also mentions extension to "groups" such as amino acid residues, but does not provide any systematic way to define such groups or how the Voronoi partition is defined in such a case.

Useful as the application of multiplets was to localized pharmocophoric interaction features, the problem remained in the prior art of how to incorporate the broader notion of shape complementarity into multiplets; that is, how to encapsulate the steric information about the whole 3-D structure of a molecule into a steric multiplet which could then be used for searching and comparison purposes. Previous attempts to incorporate steric definitions utilizing all atoms in a molecule or all heavy atoms not assigned to a pharmacophore, did not solve the problem. The present invention solves this problem through the development of a method by which multiplets encompass steric features. The inventors of the method disclosed in this patent document have determined that implementing a useful steric multiplets methodology is critically dependent upon finding an effective way of defining the steric features. The feature definitions and application to multiplet methodology constitute the basis of the present invention.

DESCRIPTION OF THE INVENTION

Figure 1:
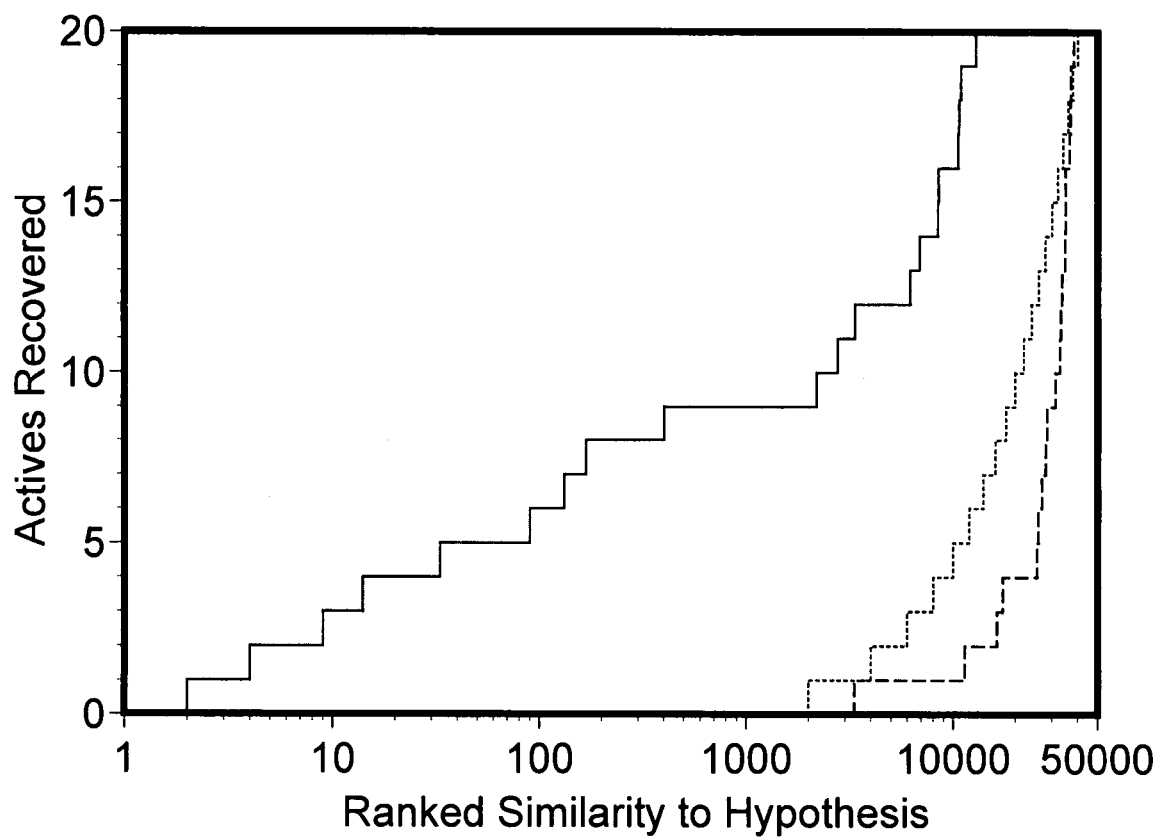
FIG. 1: Recovery curve for estrogen antagonists using steric triplets based on 100 conformations. Actives were recovered from among the approximately 44,000 decoy compounds comprising the LeadQuest® libraries. Thirteen (13) edge length bins were used, with upper bounds of 1.25 (1), 2.25 (1), 3.25 (2), 4.75 (3), 5.75 (4), 7.25 (5), 8.00 (6), 9.50 (7), 10.75 (8), 12.00 (9), 12.75 (10), 14.00 (11) and 15.00 Å (12); any edge greater than 15 Å in length (14) was assigned to a $14^{th}$ bin. The parenthetical values indicate the edge weight used to estimate the discrimination power of each triplet by summing across its constituent edges. The 100 most discriminating bits from the bitmap ensemble for the training set were used to generate the hypothesis bitmap[22] used to carry out the search.

It is useful to remember when approaching the application of multiplets to steric features that, unlike traditional molecular fingerprints or HQSAR type fingerprints where the presence of actual substructures (typically 2-7 atoms) are encoded in a bitstring, multiplets do not contain information on the individual features. Instead it is the distances between features that are specified.

A key innovative aspect of the present invention lies in how the steric features are defined. Earlier approaches used all of the atoms in a molecule to define steric features[17,18], or all heavy atoms not assigned to particular pharmacophoric features.[17] It has been discovered that using the most topologically relevant heavy atoms to define steric features gives unexpectedly superior performance, especially when the effects of bond rotation are taken into consideration.

The relevant steric definitions can be efficiently set out using the SLN language.[17] The preferred steric definitions are given below in plain English; the SLN definitions are given in Appendix "A". Alternative definitions of steric features that are based on molecular topology may be employed with the method of the present invention. For example, while the preferred embodiment defines steric features in terms of centroids of groups of heavy atoms, equivalent definitions could be written largely in terms of the hydrogens appearing in the steric features. Moreover, it should be noted that the present invention is not limited by use of SLN definitions. Other languages well known in the art could also be used.

In the definitions of steric features given here, "substituent" means any heavy (non-hydrogen) atom that is not a halogen (F, Cl, Br or I), and rules 18 through 20 apply only to atoms not "covered" by application of one of the criteria from some preceding rule.

Steric Feature Definitions:
1. a terminal heavy atom that is not a halogen—i.e., a non-hydrogen atom that is not a halogen but is bonded to exactly one other non-hydrogen atom;
2. the geometric centroid of all four atoms in terminal trihalomethanes (—$CF_3$, —$CCl_3$, —$CF_2Cl$ etc.);
3. the midpoint of the distal (unsubstituted) bond in a mono-substituted cyclopropane or cyclopropene group;
4. the distal carbon atom in a monosubstituted saturated or unsaturated cyclobutyl group;
5. the centroid of the distal 3,4-bond in 1,2-disubstituted saturated or unsaturated cyclobutyl groups;
6. the 3 and 4 atoms in monosubstituted five-membered rings, where halogens are not counted as substituents;
7. the 4-atom in 1,2-disubstituted five membered rings, where halogens are not counted as substituents;
8. the midpoint of the bond between atoms 4 and 5 in a 1,2-di- or 1,2,3-tri-substituted five-membered ring;
9. the atoms at the meta (3 and 5) positions in a mono-substituted six-membered ring;
10. both distal atoms (4 and 5 atoms) in a 1,2-disubstituted six-membered ring;
11. the distal 5 atom in a 1,3-di- or 1,2,3-tri-substituted six membered ring;
12. the midpoint of the unsubstituted bond in a 1,2,3,4-tetra- or 1,2,4-tri-substituted six membered ring, where "unsubstituted" allows for fluorine but not other halogen substitution;
13. a quaternary aliphatic carbon atom that is not in a ring and is not the central atom in a t-butyl group;
14. an alkenyl carbon that is not in a ring and is bonded to three heavy atoms, provided that the double bond is not to an oxygen atom or to a nitrogen atom;
15. a heavy atom in a ring that bears three non-aromatic bonds that are themselves in rings;
16. a heavy atom in a ring that is substituted by a non-ring heavy atom, that substituent heavy atom having no bonds to any other heavy atom;
17. a tri-substituted nitrogen not in a ring;
18. the geometric centroid of a stretch of six topologically contiguous atoms not covered by specifications 1-17, none of which are in a ring;
19. the geometric centroid of a stretch of five topologically contiguous atoms not covered by specifications 1-18, none of which are in a ring; and
20. the geometric centroid of a stretch of four topologically contiguous atoms not covered by specifications 1-19, none of which are in a ring.

Cartesian coordinates for geometric centroids are calculated by averaging the x, y and z coordinates of the specified atoms.

Encoding and Manipulation of Steric Multiplets:

A novel implementation designed to efficiently create and handle pharmacophore fingerprints as virtual bitmaps is described in detail elsewhere.[17,18] The same general approach was taken for encoding and manipulating steric multiplets. It should be noted that bitstring compression schemes have been used in the prior art for storing data, but until taught in the cited references (in part by some of the present inventors), compressed bitstrings had not been used for searching without decompression. Patterns of steric features as defined above and encoded in bitmaps have never before been used for molecular analysis or searching.

It is inefficient to generate, manipulate, or store uncompressed fingerprint bitstrings. Instead, each bitstring is represented in a compressed form known as a "bitmap" created by replacing long strings of zeros (and 1's) with an indicator of how long that string of zeros (and 1's) is. Hence the bitmap represented by 0,1000; 1,1; 0,200; 1,2; 0,100; . . .

itself represents a bitstring of one thousand zeros followed by a single 1, followed by 200 more zeros, then by two 1's and 100 zeros, and so on.

Multiplet fingerprints are characteristically rather sparse, so such compression almost always yields a considerable savings in storage space and working memory. Moreover, bitmaps can be manipulated much more efficiently than can the corresponding bitstrings, especially for the very large, very sparse fingerprints generated from pharmacophore quartets and related multiplets. This is true even for Boolean operations such as ANDing and ORing, which are very computationally efficient in other contexts. Each multiplet must map to one specific bit in the fingerprint, and it must always be possible to recover the identity of the multiplet that led to a specified bit being set in a fingerprint.

In this patent document, the term "multiplet" is used as a generic term encompassing the following multiplet classes: singlets (k=1), doublets (k=2) (pairs), triplets (k=3), quartets (k=4), and quintets (k=5) as well as higher order k-tuples which could be defined. In this disclosure "multiplet" is used in an analogous way to the sense in which multiplet is used to refer to a relationship between pharmacophore interaction features in space—that is; multiplet is a generic term for a pattern of disposition of features, irrespective of its complexity. At each vertex of a multiplet, one of the steric features defined earlier is located. It does not matter which steric feature definition is involved or what assemblage of atoms is involved since the steric features only reflect the amount of 3-D space taken up. Hence steric multiplets differ from pharmacophore multiplets in that they are treated as uncolored graphs.

A separate bitstring is generated for each type of multiplet. For multiplets of higher order than two, each multiplet can be uniquely specified by the following indexing scheme. In the present invention, each triplet is given a unique index by sorting its edges in decreasing order of bin index. Quartets are indexed by first identifying a base triangle that includes the longest and shortest edges, then appending edge bin indices in the order in which they connect the "left out" vertex to the three making up the base triangle. One possible quartet is specified by the six-dimensional index:

872 532 where [8 7 2] defines the edges for the base triangle and the other three faces of the quartet's tetrahedron can be described as triplets definable by [8 5 3], [7 5 2] and [3 2 2]. (Bracketed terms indicate vectors.) This quartet maps to exactly one bit position. Given that b edge length bins are specified, the one-dimensional index for any given bit can be found by treating the six-dimensional index as a six digit numeral in base b. If ten edge bins have been specified (b=10), for example, the [8 7 2 5 3 2] quartet cited above would map to the $872,532^{nd}$ bit. Triplets have three edges; hence their mapping is obtained by treating the specification vector as a three digit numeral. Note that the first bin specified has an index of 0 and the last bin specified has an index of (b-1) for this purpose. Encoding multiplets in this way consolidates the geometrically impossible multiplets into long stretches of zeros that are compressed out in the corresponding bitmaps.

The bitstring positions that would otherwise map back to impossible multiplets can be used to encode the chirality of quartets. The indexing described above is used if the fourth vertex lies to the "right" of the base triangle, whereas the edge indexing of the base triangle is inverted if the fourth vertex lies to the "left." Hence the left-handed version of the quartet described above would be:

278 235

Note that the inverted order of the initial edge indices immediately identifies this as the definition of a "left handed" quartet.

Besides facilitating compression, this coding scheme is readily extensible to accommodate a broad range of hybrid multiplets. For instance, the fourth vertex in a quartet can be assigned to a specific substructure previously identified as important for binding, e.g., a privileged substructure[22] such as a hydroxamic acid or sulfonamide group involved in binding to Zn metalloproteins. Bitmaps (or fingerprints) based on such hybrid multiplets composed of a pharmacophoric feature or a privileged substructure as well as steric features can be more effective analysis tools than either "pure" type of bitmap or by simply adding steric features to the list of definitions used to generate pharmacophoric feature multiplets.

Drug-like molecules usually bear a fair number of steric features, so the number of bits set in a multiplet generally increases as the dimensionality of the multiplet increases— i.e., there are more quartets than triplets, and more triplets than doublets. The number increases more slowly, however, than does the number of possible multiplets, which is what dictates the length of the corresponding fingerprint. The net result is that the corresponding fingerprints grow progressively more sparse and the growth in bitmap size can be handled without having to set artificial limits on the number of distance bins allowed.

It should also be noted that one can speak of a pharmacophore as meaning a structural feature found in the 20 definitions set out above. Molecular substructures that define traditional pharmacophoric interaction features can overlap. However, the steric pharmacophore features defined for this invention are designed not to overlap, that is: they define a true volume voxel.

Once the bitmaps are generated, many different types of searches may be employed. While the following list is not inclusive of all types of searches that may be performed using the steric multiplet bitmaps, the bitmaps will be particularly useful for conducting the following types of investigations:

1. steric bitmap hypotheses plus multiple conformers for database searching
2. steric bitmaps for comparing single conformations of different molecules
3. steric bitmaps for assessing similarity to a binding site hypothesis
4. steric bitmaps for assessing similarity to an hypothesis based on multiple ligands
5. steric bitmaps for assessing molecular diversity
6. mixed multiplet bitmaps in which one feature is a specific substructure and two or three are steric features
7. mixed multiplet bitmaps in which one is a steric feature and two or three are pharmacophoric features Using the bitmaps (or fingerprints) for searching can be accomplished with many of the prior art fingerprint search methodologies. However, in the preferred method of this invention the following searching/comparison methodology is particularly advantageous.

Similarity Measures:

Earlier tools for generating and manipulating multiplet fingerprints were predicated on the assumption that "complete" conformational sampling could be achieved by starting from single 3-D structures created using a rule-based system, then applying large torsional increments to each bond. The approach had the added virtue of being nominally deterministic. As noted above, however, it is likely to be adequate only for bonds between pairs of $sp^3$ atoms. We chose to make the means of evaluating similarity independent of the way in which the conformers were generated. Hence a new similarity measure, the Stochastic Cosine[22], was developed that is applicable when the conformational sampling method used is stochastic in nature:

$$C*(a, b) = \frac{E(|a \cap b|)}{\sqrt{E(|a \cap a'|) \times E(|b \cap b'|)}}$$

Here, a and a' correspond to multiplets summed across different samples from one conformational population, whereas b and b' represent multiplets for samples drawn from a different population (e.g., for a different molecule). The vertical bars indicate application of the cardinality operator, and E indicates that an expectation is being taken. For determinate cases, a and a' are identical, as are b and b', so the expression reduces to the well-known cosine similarity coefficient.

Generating a multiplet hypothesis involves truncating a fingerprint rather severely by discarding the less discriminating bits. This can distort symmetrical similarity coefficients like the Stochastic Cosine. It is often more appropriate when a represents a multiplet hypothesis to use the Asymmetric Stochastic Cosine defined by:

$$A*(a, b) = \frac{E(|a \cap b|)}{E(|a \cap a'|)}$$

In part to accommodate such stochastic considerations, each multiplet file is, by default, actually made up of four separate bitmaps: the intersection across all conformers, the union across all conformers, and the unions across each of two subsets obtained by random assignment of the conformers fed into the program. The infrastructure supports any number of subsets, however, which could be useful in conformational analysis and other applications.

EXAMPLE

Steric triplet bitmaps were constructed for twenty known estrogen antagonists taken from the open literature.[22] A steric multiplet hypothesis was then constructed from the 100 most discriminating triplets common among them, with 100 conformers examined for each molecule. This hypothesis was then applied to a database constructed by adding those twenty compounds to approximately 42,000 decoy drugs and drug-like structures drawn from LeadQuest® libraries distributed by Tripos with ®UNITY® 3.3. The recovery curve obtained using steric triplets is represented by the solid line in FIG. 1, along with the recovery curve obtained using all heavy atoms as steric features (dashed line) and the recovery curve expected for random selection (dotted line). Note that using all heavy atoms gives results significantly inferior to random selection.

The corresponding pharmacophore triplet query showed very similar discrimination, identifying roughly half of the known actives in the top 2.5% of the database screened.[22] The training set used to generate the steric query used here is the same as that used for the pharmacophore experiment, but the target database screened is quite different—primarily the LeadQuest® libraries rather than the Novo Nordisk corporate database. This suggests that the qualitative similarity in the results seen here is a property of the structural diversity of the training set rather than of the descriptors, a supposition that is supported by clustering results.

The method of encapsulating steric information in steric multiplets for generating bitmaps (or bitstrings) has a broad range of applicability for comparing molecules and searching assemblages of molecular structures based on their three dimensional shapes. While specific steric feature definitions have been set forth above, those skilled in the art will appreciate that, with the guidance provided by this disclosure, other definitions could be created based on similar topological considerations and used with multiplets and such are considered within the teachings of this patent document. Use of multiplets based on steric feature definitions identical to or analogous to those taught in this disclosure for searching are all considered within the teachings of this patent document.

REFERENCES

1. P. Gund; Evolution of the Pharmacophore Concept in Pharmaceutical Research. In: *Pharmacophore Perception, Development and Use in Drug Design*, O. F. Güner (Ed.); International University Line, La Jolla Calif., 2000; pp. 1-11.
2. D. D. Beusen & G. R. Marshall; Pharmacophore Definition Using the Active Analog Approach. In: *Pharmacophore Perception, Development and Use in Drug Design*, O. F. Güner (Ed.); International University Line, La Jolla Calif., 2000; pp. 21-45.
3. Available commercial 3D pharmacophore searching software is currently dominated by UNITY (Tripos, Inc., 1699 S. Hanley Rd., St. Louis Mo. 63144; http://www.tripos.com) and CATALYST (Accelrys, Inc., 9685 Scranton Road, San Diego, Calif. 92121; http://www.accelrys.com).
4. A. V. Ishchenko & E. I. Shakhnovich. SMall Molecule Growth 2001 (SMoG2001): An Improved Knowledge-Based Scoring Function for Protein-Ligand Interactions. *J. Med. Chem.* 2002, 45, 2770-2780.
5. P. A. Greenidge, B. Carlsson, L.-G. Bladh & M. Gillner. Pharmacophores Incorporating Numerous Excluded Volumes Defined by X-ray Crystallographic Structure in Three-Dimensional Database Searching: Application to the Thyroid Hormone Receptor. *J. Med. Chem.* 1998, 41, 2503-2512.
6. M. Gillner & P. Greenidgel; The Use of Multiple Excluded Volumes Derived from X-Ray Crystallographic Structures in 3D Database Searching and 3D QSAR. In: *Pharmacophore Perception, Development and Use in Drug Design*, O. F. Güner (Ed.); International University Line, La Jolla Calif., 2000; pp. 372-384.
7. T. Hurst. Flexible 3D Searching: The Directed Tweak Technique. *J. Chem. Inf. Comput. Sci.* 1994, 34, 190-196.
8. S. D. Pickett, C. Luttmann, V. Guerin, A. Laoui & E. James. DIVSEL and COMPLIB —Strategies for the Design and Comparison of Combinatorial Libraries using Pharmacophoric Descriptors. *J. Chem. Inf. Comput. Sci.* 1998, 38, 144-150.
9. E. J. Martin & T. J. Hoeffel. Oriented Substituent Pharmacophore PRopErtY Space (OSPREYS): A substituent-based calculation that describes combinatorial library products better than the corresponding product-based calculation. *J. Mol. Graph. Model.* 2000, 18, 383-403.
10. M. J. McGregor & S. M. Muskal. Pharmacophore Fingerprinting. 2. Application to Primary Library Design. *J. Chem. Inf. Comput. Sci.* 2000, 40, 117-125.
11. S. D. Pickett, Jonathan S. Mason & I. M. McLay. Diversity Profiling and Design Using 3D Pharmacophores: Pharmacophore-Derived Queries (PDQ). J. Chem. Inf. Comput. Sci. 1996, 36, 1214-1223.
12. D. E. Patterson, R. D. Cramer, R. D. Clark & A. M. Ferguson. A method for selecting an optimally diverse library of small molecules based on validated molecular structural descriptors. U.S. Pat. No. 6,185,506 (2001).
13. R. D. Cramer, R. D. Clark, D. E. Patterson & A. M. Ferguson. Bio-isosterism as a molecular diversity descriptor: steric fields of single "topomeric" conformers. *J. Med. Chem* 1996, 39, 3060-3069.
14. R. D. Clark, A. M. Ferguson & R. D. Cramer. Bioisosterism and molecular diversity. In: *3D QSAR in Drug Design*, Vol 2; H. Kubinyi, Y. C. Martin & G. Folkers, Eds.; Kluwer Academic, Dordrecht, the Netherlands, 1998; pp 211-224.
15. http://www.ics.uci.edu/~eppstein/gina/voronoi.html
16. http://cage.ugent.be/~dc/alhtml/Delaunay.html
17. R. Nilakantan, N. Bauman & R. Venkataraghavan. New Method for Rapid Characterization of Molecular Shapes: Applications in Drug Design. *J. Chem. Inf. Comput. Sci.* 1993, 33, 79-85.
18. A. C. Good, T. J. A. Ewing, D. A. Gschwend & I. D. Kuntz. *J. Comput.-Aided Mol. Design* 1995, 9, 1-12.
19. M. J. McGregor & S. M. Muskal. Pharacophore Fingerprinting. 1. Application to QSAR and Focused Library Design. J. Chem. Inf. Comput. Sci. 1999, 39, 569-574.
20. S. Ash, M. A. Cline, R. W. Homer, T. Hurst & G. B. Smith. SYBYL Line Notation (SLN): A Versatile Language for Chemical Structure Representation. *J. Chem. Inf. Comput. Sci.* 1997, 37, 71-79.
21. P Fox, E Abrahamian, R D Clark, I T Christensen, H Thøgersen. Fully flexible pharmacophore multiplet bitmaps as molecular descriptors: implementation and applications. 225th ACS National Meeting, New Orleans, 2003, COMP 377.
22. E Abrahamian, P C Fox, L Naerum, I T Christensen, H Thøgersen, R D Clark. Efficient generation, storage and manipulation of fully flexible pharmacophore multiplets and their use in 3-D similarity searching. J Chem Inf Comput Sci 43:458-468, 2003.

---

APPENDIX "A"

SLN definitions of steric features
define:: Steric_Feature[name; target; rules; connection]

APPENDIX "A"

```
# Terminal Heavy Atoms
centroid[name=::name::_ST_1;
        sln=Hev[HAC=1¬=Hal];
        features=1;
        comment="Terminal non-Halogen Heavy atom w_1 non H bond"]
# Tri halo methanes
centroid[name=::name::_ST_2;
        sln=C(Hal)(Hal)Hal;
        features=1,2,3,4;
        comment="Centroid of CHal3"]
# "Terminal" Ring Atoms
# 3 membered rings (cyclopropane, cyclopropene)
#    Midpoint of outer bond
centroid[name=::name::_ST_3;
        sln=C[1:HAC=3]-=Z-=Z@1{Z:C[HAC=2]};
        features=2,3;
        comment="Cycylpropane or Cycylpropene rings"]
#    Both Outer Atoms?
#centroid[name=::name::_ST_3;
#        sln=C[1:HAC=3]Z-=Z@1{Z:C[HAC=2]};
#        features=2;
#        comment="Cyclopropane outer atoms"]
# 4 membered rings (Hydrocarbon)
# Single attachment
centroid[name=::name::_ST_4;
        sln=C[1:HAC=3]-=Z-=Z-=Z@1{Z:C[HAC=2]};
        features=3;
        comment="Cyclobutyl Rings pendant"]
# 2 attachments
centroid[name=::name::_ST_5;
        sln=C[1:HAC=2]-=C[HAC=2]-=C[HAC=3]~C[HAC=3]@1;
        features=1,2;
        comment="Cybylbutyl Ring Fused"]
# 5 membered rings
#    Pendant rings to give 3,4 terminal atoms
centroid[name=::name::_ST_7;
        sln=Hev[1:HAC=3]~Z~Z~Z~Z~@1{Z:Hev[is=Hev[HAC=2],Hev[HAC=3]Hal]};
        features=3;
        comment="pendant 5 membered ring"]
#        1,2 substituted 5 membered ring to give 4 terminal atom
centroid[name=::name::_ST_8;
        sln=Zz[1]~Zz~Z~Z~Z~@1{Zz:Hev[HAC=3¬=HevHal]}\
{Z:Hev[is=Hev[HAC=2],Hev[HAC=3]Hal]};
        features=4;
        comment="1,2 disubstituted 5 membered ring"]
#        1,3 or 1,2,3 substituted 5 membered fing to give 4-5 bond midpoint site
centroid[name=::name::_ST_12;
        sln=Zz[1]~Hev~Zz~Z~Z~Z~@1{Zz:Hev[HAC=3¬=HevHal]}\
{Z:Hev[is=Hev[HAC=2],Hev[HAC=3]Hal]};
        features=4,5;
        comment="1,3 disubstituted 5 membered ring"]
# 6 membered Rings
# Pendant 6 membered ring to give 3,4,5 terminal atoms
centroid[name=::name::_ST_9;
        sln=Zz[1]~Z~Z~Z~Z~Z~@1{Zz:Hev[HAC=3]}\
{Z:Hev[is=Hev[HAC=2],Hev[HAC=3]Hal]};
        features=3;
        comment="pendant 6 membered ring meta atoms"]
# Uncomment to give the para (4) atom marked in pendant 6 membered rings
#centroid[name=::name::_ST_9a;
#        sln=Zz[1]~Z~Z~Z~Z~Z~@1{Zz:Hev[HAC=3]}\
{Z:Hev[is=Hev[HAC=2],Hev[HAC=3]Hal]};
features=4;
#        comment="pendant 6 membered ring para atom"]
#    1,2 substituted 6 membered ring to give 4,5 atoms
centroid[name=::name::_ST_10;
        sln=Zz[1]~Zz~Z~Z~Z~Z~@1{Zz:Hev[HAC=3¬=HevHal]}\
{Z:Hev[is=Hev[HAC=2],Hev[HAC=3]Hal]};
        features=4;
        comment="1,2 disubstituted 6 membered rings 4,5 points"]
#    1,3 disubstitution to give terminal 5 atom
#    Modification to work with 1,2,3 substitution patterns as well
centroid[name=::name::_ST_11;
        sln=Zz[1]~Hev~Zz~Z~Z~Z~@1{Zz:Hev[HAC=3¬=HevHal]}\
{Z:Hev[is=Hev[HAC=2],Hev[HAC=3]Hal]};
        features=5;
        comment="1,3 disubstituted 6 membered ring terminal 5"]
```

-continued

APPENDIX "A"

```
#    1,2,3,4 substituted systems to mark 5,6 bond midpoint
#    Modified to work with 1,2,4 substitution patterns as well
centroid[name=::name::_ST_6;
        sln=Zz[1]~Hev~Zz~Zz~Z~Z~@1{Zz:Hev[HAC=3¬=HevHal]}\
{Z:Hev[is=Hev[HAC=2],Hev[HAC=3]F]};
        features=5,6;
        comment="5,6 unsubstituted 6 membered rings mid 5,6 bond "]
#    1,2,3,4 substituted systems to mark 5,6 bond midpoint
#    Alternative definition that works with 1,2,4 and 1,4 substitution patterns as well
# centroid[name=::name::_ST_6;
#            sln=Zz[1]~Hev~Hev~Zz~Z~Z~@1{Zz:Hev[HAC=3¬=HevHal]}\
# {Z:Hev[is=Hev[HAC=2],Hev[HAC=3]F]};
features=5,6;
comment="5,6 unsubstituted 6 membered rings mid 5,6 bond "]
# Branching points for Carbon
#    sp3_Alkyl excluding t-bu carbons
centroid[name=::name::_ST_13;
        sln=C[is=C[!R](Hev)(Hev)Hev¬=C(CH3)(CH3)CH3];
        features=1;
        comment="sp_3 Alkyl Branching Carbon"]
#    sp2_Alkyl chain
centroid[name=::name::_ST_14;
        sln=C[is=C[!r](=Hev[not=O,N])(Hev)Hev];
        features=1;
        comment="sp_2 Branching Carbon not ring"]
#    non-Aromatic Ring Fusion
centroid[name=::name::_ST_15;
        sln=Hev[is=Hev[R](~[R&!type=:]Hev[R])(~[R&!type=:]Hev[R])~[R&!type=:]Hev[R]];
        features=1;
        comment="non-Aromatic Ring Fusion"]
#    Ring Substitution points discarding OH Me NH2 =O Hal substitutions
centroid[name=::name::_ST_16;
        sln=Hev[is=Hev*(~[!R]Hev[not=Hal,OH,CH3,N[HAC=1],O[TAC=1]])\
(~[R]Hev)~[R]Hev];
        features=1;
        comment="Ring Branch Points"]
# Nitrogen specific Branching Atoms
#    NR3:
centroid[name=::name::_ST_17;
        sln=N[is=N[!R](Hev)(Hev)Hev];
        features=1;
        comment="NR3 Branching point"]
# Internal Chain steric Features
centroid[name=::name::_ST_18;
sln=Hev[c=o;n]~Z[c=n;n]~Z[c=n;n]~Z[c=n;!n]~Z[c=n;!n]~Z[c=n;n]\
~Z[c=n;n]~Hev[n]{Z:Hev[!R;is=Hev[HAC-2]]};
        features=2,3,4,5,6,7;
        comment="6 atoms in a straight chain "]
centroid[name=::name::_ST_19;
        sln=Hev[c=o;n]~Z[c-n;!n]~Z[c=n;!n]~Z[c=n;!n]~Z[c=n;!n]~Z[c=n;!n]\
~Hev[c=o;n]{Z:Hev[!R;is=Hev[HAC=2]]};
        features=2,3,4,5,6;
        comment="5 atoms in a straight chain "]
centroid[name=::name::_ST_20;
        sln=Hev[c=o;n]~Z[c=n;!n]~Z[c=n;!n]~Z[c=n;!n]~Z[c=n;!n]~Hev[c=o;n]\
{Z:Hev[!R;is=Hev[HAC=2]]};
        features=2,3,4,5;
        comment="4 atoms in a straight chain"]
or[name=::name::;
::if:target::
    target=::target::;
::endif::
    features=::name::_ST_1,
            ::name::_ST_2,
            ::name::_ST_3,
            ::name::_ST_4,
            ::name::_ST_5,
            ::name::_ST_6,
            ::name::_ST_7,
            ::name::_ST_8,
            ::name::_ST_9,
            ::name::_ST_10,
            ::name::_ST_11,
            ::name::_ST_12,
            ::name::_ST_13,
            ::name::_ST_14,
            ::name::_ST_15,
```

| -continued |
| :---: |
| APPENDIX "A" |

```
            ::name::_ST_16,
            ::name::_ST_17,
            ::name::_ST_18,
            ::name::_ST_19,
            ::name::_ST_20;
# segment_size=12;
# segment_rules=IS_1,IS_2;
# segment_exclude_sln=Any[is=Hev[R],H];
::if:rules::
      rules=::rules::;
::endif::
      screen=Steric_Feature]
end_define
```

We claim:

1. A computer implemented method for identifying the candidate molecule or molecules in a large array of molecules that are similar in three dimensional shape to query molecules, comprising the following steps:

a) defining a set of topologically distinct steric features that taken together cover the substructures found in each molecule;

b) identifying the positions of the steric features in each conformer of a query molecule;

c) selecting a class of multiplet for use;

d) using the selected multiplet class, for each query molecule, identifying the multiplet or multiplets that occur within at least one conformer of the molecule;

e) dividing the set of conformations for each query molecule into at least two subpopulations by randomly assigning each conformer to one subpopulation;

f) creating bitmaps indicating which multiplets occur in each conformer subpopulation of each molecule;

g) logically ORing the bitmaps of each conformer for each molecule;

h) generating a steric multiplet hypothesis by identifying discriminating multiplets from the bitmaps based upon how many conformers each multiplet occurs in and the size of the multiplet;

i) identifying the positions of the steric features in each conformer of the molecules in the large array;

j) using the previously selected multiplet class, for each molecule in the array identifying the multiplet or multiplets that occur within at least one conformer of the molecule;

k) creating bitmaps indicating which multiplets occur in each conformer of each molecule;

l) logically ORing the bitmaps of each conformer for each molecule; and m) comparing the bitmap for each array molecule to the steric multiplet hypothesis bitmap to determine those array molecules most similar in three dimensional shape to the query molecule.

2. The method of claim 1 in which the selected multiplet class is chosen from either steric or pharmacophore-dependent multiplets.

* * * * *